US009436798B2

(12) United States Patent
Lobregt et al.

(10) Patent No.: US 9,436,798 B2
(45) Date of Patent: Sep. 6, 2016

(54) METHOD OF RETRIEVING DATA FROM A MEDICAL IMAGE DATA SET

(75) Inventors: Steven Lobregt, Eindhoven (NL); Joost Frederik, Eindhoven (NL); Alan Pek Seng Tjhang, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 573 days.

(21) Appl. No.: 12/746,932

(22) PCT Filed: Dec. 5, 2008

(86) PCT No.: PCT/IB2008/055110
§ 371 (c)(1),
(2), (4) Date: Jun. 9, 2010

(87) PCT Pub. No.: WO2009/074930
PCT Pub. Date: Jun. 18, 2009

(65) Prior Publication Data
US 2010/0266174 A1    Oct. 21, 2010

(30) Foreign Application Priority Data
Dec. 13, 2007  (EP) .................................. 07123160

(51) Int. Cl.
*G06K 9/00* (2006.01)
*G06F 19/00* (2011.01)

(52) U.S. Cl.
CPC ................................ *G06F 19/321* (2013.01)

(58) Field of Classification Search
None
See application file for complete search history.

(56) References Cited

U.S. PATENT DOCUMENTS

| 2005/0276455 | A1 | 12/2005 | Fidrich et al. |
| 2006/0085407 | A1 | 4/2006 | Kaminaga et al. |
| 2006/0155577 | A1* | 7/2006 | Niemeyer ........................ 705/2 |
| 2007/0049817 | A1 | 3/2007 | Preiss et al. |

FOREIGN PATENT DOCUMENTS

| EP | 1182585 A2 | 2/2002 |
| WO | 2006085257 A2 | 8/2006 |

(Continued)

OTHER PUBLICATIONS

Xu et al: "Image Segmentation Using Deformable Models"; Chapter 3 (pp. 129-174) of the "Handbook of Medical Imaging, vol. 2:Medical Image Processing and Analysis", SPIE Press, May 2000.

(Continued)

*Primary Examiner* — Stephen R Koziol
*Assistant Examiner* — Raphael Schwartz

(57) ABSTRACT

The present invention discloses a method of retrieving a plurality of data slices from a medical image data set (5), the method comprising the steps of: a) displaying an indicator (10, 20) associated with the plurality of data slices; b) selecting the indicator (10, 20) based on a user input; and c) retrieving the plurality of data slices (1, 2) associated with the indicator when said indicator is selected; wherein the association between the indicator and the plurality of slices is based on segmentation of the medical image data set, the indicator representing an object obtained in the segmentation of the medical image data set, the plurality of data slices comprising the object data. The method of the invention reduces the amount of data transfer because it allows for retrieving only those data slices which comprise relevant data relating to the object of interest.

20 Claims, 6 Drawing Sheets

(56) References Cited

FOREIGN PATENT DOCUMENTS

| WO | 2007026951 A1 | 3/2007 |
| WO | WO 2007056601 A2 * | 5/2007 |

OTHER PUBLICATIONS

Sample of an Interactive Brain Atlas From the University of Washington That Gives Thumbnail Images of Various Parts of Brains. Downloaded From http://da.biostar.washington.edu/cgi-bin/da/imageform; 2 Pages, Aug. 17, 2007.

Sample of an Interactive Program Downloaded From http://www.med.harvard.edu/AANLIB/cases/case5/mr2/020.html on Aug. 20, 2007. 1 page.

"How to Use the Medisurf Image Viewer"; IU Radiology Physics; Instructions on How to Retrieve Patient Images From the Medisurf Image Viewer, Downloaded From http://www.indyrad.iupui.edu/RadWeb/Portals/0/Content Files/CNS/SystemInstruction/Medisurf on Aug. 20, 2007, 3 Pages.

Reddy et al:"Content Based Image Retrieval Using Region Labelling"; Computer Vision, Graphics and Image Processing. 5th Indian Conference, ICVGIP 2006, LNCS, vol. 4338, pp. 872-881.

Long et al: "Image Informatics at a National Research Center"; Computerized Medical Imaging and Graphics vol. 29 (2005), pp. 171-193.

Sasso et al: "A Visual Query-By Example Image Database for Chest CT Images: Potential Role as a Decision and Educational Support Tool for Radiologists"; Journal of Digital Imaging, vol. 18, No. 1, Mar. 2005, pp. 78-84.

\* cited by examiner

A:  B:  C:

10 HEART

20 LUNG

FIG. 6

METHOD OF RETRIEVING DATA FROM A MEDICAL IMAGE DATA SET

FIELD OF THE INVENTION

The present invention relates to a method of retrieving data from a medical image data set obtained from a medical imaging modality. The invention also relates to a corresponding system for implementing the method, and a corresponding computer program product for such an implementation.

BACKGROUND OF THE INVENTION 3D medical image data is often acquired in the form of a set of slices of data. The set of slices defines volumetric, i.e. 3D, image data. This set may be referred to as an image data set or just as image data. The most common way of inspecting a large 3D medical data set from e.g. a CT scanner or similar device, is to load a data set from a storage medium and to display cross-sectional slices of that volume. The locations of interest in that volume are found by scrolling through the (often large number of) slices. Normally, this is the stack of original slices as they come from the acquisition device. This is a quite time consuming task, which includes navigating to the areas of interest and visually inspecting the slices. When inspecting the data like this, there is no help or assistance available to facilitate or accelerate finding of the target locations.

Thus, current procedure is to retrieve the complete data set, navigate through the acquired slices to locate an area or object of interest, inspect this area of interest, and navigate from one area of interest to the next by scrolling through the data when more then one object needs to be inspected.

Alternatively, when the user knows in which part of the data set the object of interest can be expected, a part of the data set can be retrieved. This requires however that the user inspects a number of thumbnail representations of slices at regular intervals in the data set, and decides which interval(s) to retrieve.

If multiple objects need to be inspected, the user will in general have to retrieve the whole data set or a part of it, navigate to a first area of interest, and locally scroll through slices that contain parts of this first object. After that the user will navigate to a next area of interest to inspect the next object, etc, until all objects have been inspected. Because there is no information available about the locations and sizes etc. of the objects relative to the data set, all of the data set has to be retrieved. Alternatively, a user may spend time on selecting a part of the data set that in any case covers a larger volume than the object(s) of interest.

All applications that require retrieving data from large data sets, for inspection of objects that are represented by parts of those data sets, take time. The number of slices that hold cross-sections with an object of interest can be much smaller that the total number of slices in a data set. Loading large data sets takes even more time, which is annoying for the user. If only a relatively small part of the data set is required, because the area of interest is much smaller that the complete covered volume, time and computer resources are wasted.

The problem of (nearly) useless data retrieval is becoming more and more pressing due to the increasing spatial resolution of current medical imaging modalities. Thus, previously maybe around 100-200 slices were obtained from an imaging session, now the number can typically be above 1000 slices, making manual analysis of such an amount of slices quite time consuming.

Current techniques for representing a large amount of data and giving a user an improved overview of the medical image data set can be found in for example US 2006/0085407, where a one-line list or thumbnails is used to give an overview of a large data set. However, the thumbnail pictures are chosen based on a numbering of the slices or pictures, which is not very effective for selecting relevant anatomical parts in the region of interest.

Hence, an improved method of retrieving data from a medical image data set would be advantageous, and in particular a more efficient and/or reliable method would be advantageous.

SUMMARY OF THE INVENTION

Due to the increasing demand for medical image analysis, there has recently been a growth in systems that can provide automatic methods of (rough) segmentation of the objects in this medical data set, so that the approximated boundary and occupied volume is known for a number of objects. This information can be used for 'content aware viewing'. In the case of a medical data set, the objects could be different organs that are present in the volume covered by the data set, and that are detected, identified and roughly segmented, like lungs, heart, liver, spleen, kidneys. Automatic methods of segmentation and recognition of the different objects that are present in a data set are already available, and although they do not always work perfectly, they are rapidly being further developed and emerging in the field. The results of such a method can be available and stored with the data set and include object-specific information like name, segmented volume, appearance properties, abnormalities in shape or location, etc. The content information can be extracted automatically at acquisition time or at first access of the data.

Thus, automatic segmentation and content analysis can be found in e.g. US 2005/0276455. For a general review of segmentation in medical imaging, the reader is referred to C. Xu, D. Pham, and J. L. Prince, "Medical Image Segmentation Using Deformable Models," *Handbook of Medical Imaging*, Volume 2: Medical Image Processing and Analysis, pp. 129-174, edited by J. M. Fitzpatrick and M. Sonka, SPIE Press, May 2000.

Accordingly, the invention preferably seeks to mitigate, alleviate or eliminate one or more of the above mentioned disadvantages either singly or in any combination. In particular, it may be seen as an object of the present invention to provide a method of easier and/or faster retrieving of representative data from a medical image data set.

This object and several other objects are achieved in a first aspect of the invention by providing a method of retrieving a plurality of data slices from a medical image data set, the method comprising:
a) displaying an indicator associated with the plurality of data slices;
b) selecting the indicator based on a user input; and
c) retrieving the plurality of data slices associated with the indicator when said indicator is selected;
wherein the association between the indicator and the plurality of slices is based on segmentation of the medical image data set, the indicator representing an object obtained in the segmentation of the medical image data set, the plurality of data slices comprising the object data.

The invention is particularly, but not exclusively, advantageous for obtaining a method where a user may have an improved overview of a relatively large medical image data set. Additionally, the method may provide shorter user waiting times, because a user does not have to wait for a large data set to be retrieved since the representative indicator is typically only a fractional size of the data set. Also, the user does not have to scroll forward and backward through the acquired slices to locate the slices related to an area or region of interest (ROI).

In a preferred embodiment, the method may further comprise:

segmenting the medical image data, thereby obtaining the object data;

identifying slices comprising the object data, thereby creating the plurality of data slices;

determining the indicator to be associated with the plurality of data slices; and associating the indicator with the plurality of data slices.

In one embodiment, the indicator may be a picture representative of the object, based on a slice from the plurality of slices. Preferably, the picture may be a thumbnail picture or another small scale picture, so that many pictures may be displayed on a display and viewed by a user. Additionally, or alternatively, the first and second indicator may be a representative text describing the plurality of slices. The text is most suitable in a generally accepted language in the field, e.g., Latin or a language commonly spoken in the geographical area/region of application.

The segmentation may be based on a plurality of slices through the medical image data set, although another segmentation method, such as segmentation based on detecting a contour in an image computed from a single data slice, may also be implemented in the method of the present invention. Moreover, the indicator may be based on representative slices from the plurality of data slices. The representative slices may preferably be shown reduced in size, e.g. as thumbnails. In possible variations of the present invention, the indicator may be based on any data subset, e.g. a cubic or circular data subset, of the medical image data set under examination. Possibly, the indicator may be based on a slice chosen approximately from the middle of the plurality of data slices.

In one embodiment, the object is an anatomically distinct region, i.e. distinct from the remaining volume in the plurality of slices. Additionally, or alternatively, the object may be found from a content-specific analysis comprising an anatomical recognition method.

In one embodiment, the indicator may be selected from a cross-sectional view comprising one or more principal axes of the object, e.g. of the moment of inertia tensor of the object. Thus, various considerations may influence the choice of an indicator.

In another embodiment, the indicator associated with the plurality of slices may be selected from a table with pre-defined indicator. The table may contain a pre-defined list of symbols, each symbol having a given meaning, preferably a generally accepted meaning in the field of medicine. Alternatively, the table may contain settings for creating an indicator. For example, when a heart is detected, the indicator view can be set for displaying four chambers.

In a second aspect, the present invention relates to a system for retrieving a plurality of data slices from a medical image data set, the system comprising:

a) an indicator unit for displaying an indicator associated with the plurality of data slices;

b) a selection unit for selecting the indicator based on a user input; and c) a retrieval unit for retrieving the plurality of data slices associated with the indicator when said indicator is selected;

wherein the association between the indicator and the plurality of slices is based on segmentation of the medical image data set, the indicator representing an object obtained in the segmentation of the medical image data set, the plurality of data slices comprising the object data.

Preferably, the system may further comprise:

a segmentation unit for segmenting the medical image data, thereby obtaining the object data;

an identification unit for identifying slices comprising the object data, thereby creating the plurality of data slices;

a determination unit for determining the indicator to be associated with the plurality of data slices; and an association unit for associating the indicator with the plurality of data slices.

In a fourth aspect, the invention relates to an image acquisition apparatus comprising a system according to the third aspect.

In a fifth aspect, the invention relates to a computer program product being adapted to enable a computer system comprising at least one computer having data storage means in connection therewith to control a computer system according to the first aspect of the invention.

This aspect of the invention is particularly, but not exclusively, advantageous in that the present invention may be accomplished by a computer program product enabling a computer system to carry out the operations of the first aspect of the invention when the computer program product is down- or up-loaded into the computer system. Such a computer program product may be provided on any kind of computer readable medium, or through a network.

The individual aspects of the present invention may each be combined with any of the other aspects. These and other aspects of the invention will be apparent from the following description with reference to the described embodiments.

BRIEF DESCRIPTION OF THE FIGURES

The invention will now be described in more detail with regard to the accompanying figures. The figures show one way of implementing the present invention and are not to be construed as being limiting to other possible embodiments falling within the scope of the attached claim set.

FIG. 6 illustrates a portion of a user interface according to the present invention.

DETAILED DESCRIPTION OF AN EMBODIMENT

Figure 1:
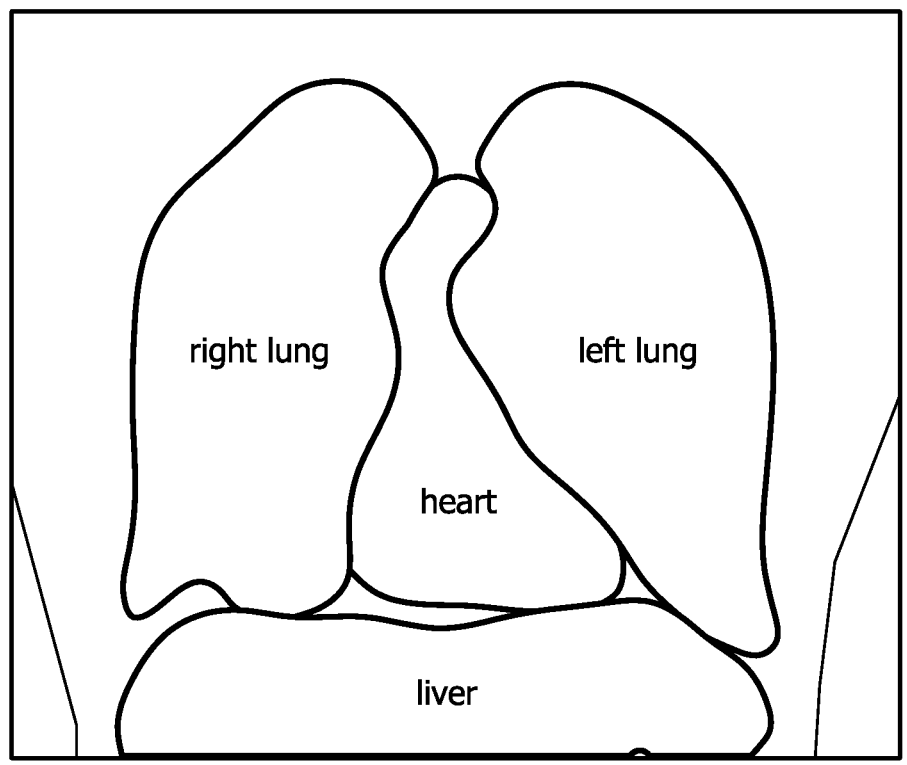
FIG. 1 shows a schematic drawing of various organs found from a content aware analysis of the thorax and upper abdomen.

FIG. 1 shows a schematic drawing of various organs found from a content aware analysis of the upper abdomen and the thorax of a human being (homo sapiens). In currently available systems for performing a content specific analysis with a semi-automated/automated anatomical recognition method, it is possible to analyze and recognize organs like lungs (left and right), heart, and liver (all three organs shown in FIG. 1), but also spleen, spinal cord, brain, bladder, colon, vessel structures in general, and kidneys are presently detectable from a medical image data set 5. For general reference to segmentation in medical imaging, the reader is referred to C. Xu, D. Pham, and J. L. Prince, "Medical Image Segmentation Using Deformable Models," *Handbook of Medical Imaging*, Volume 2: Medical Image Processing and Analysis, pp. 129-174, edited by J. M. Fitzpatrick and M. Sonka, SPIE Press, May 2000, which is hereby incorporated by reference in its entirety.

Figure 2:
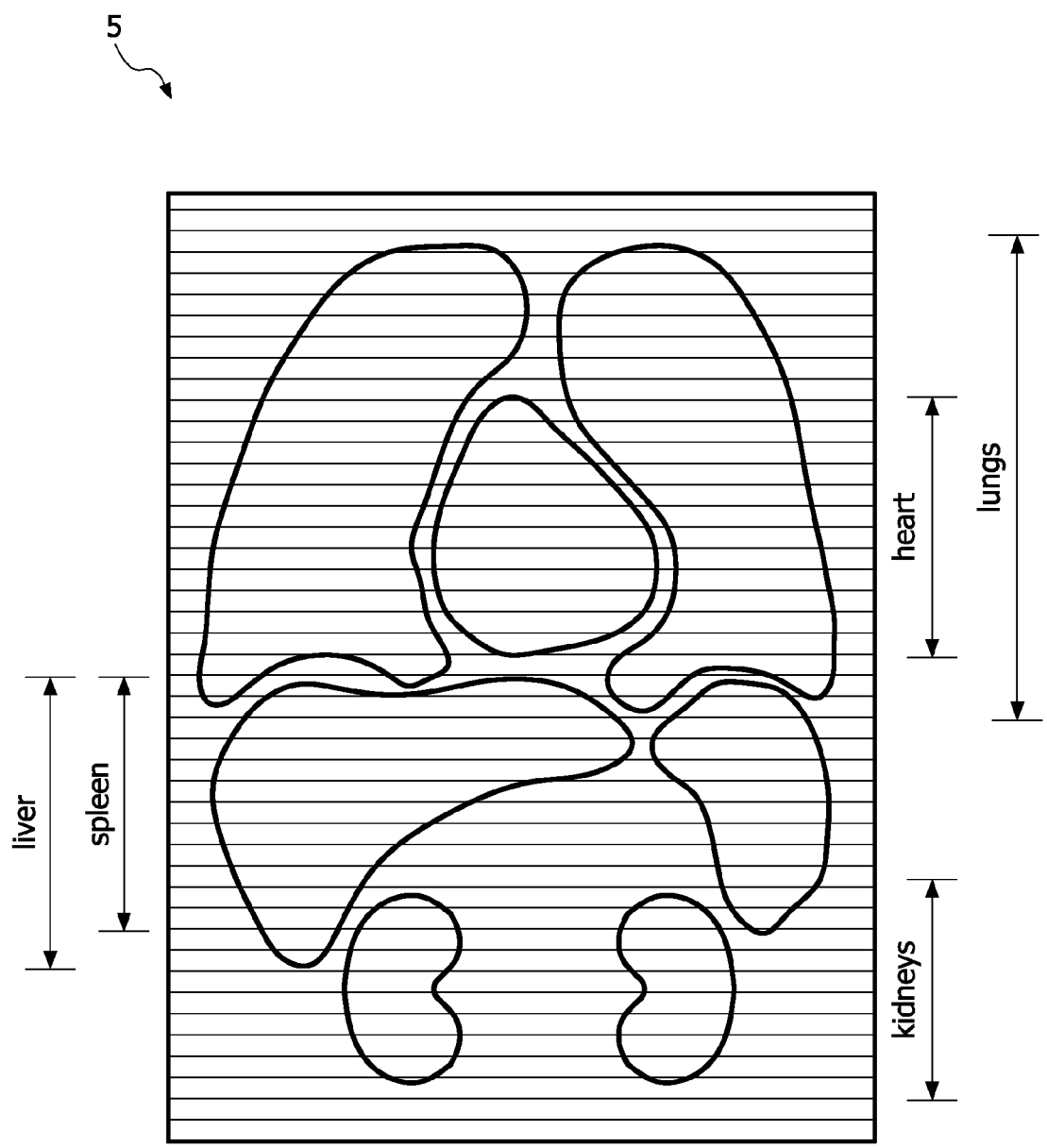
FIG. 2 shows a schematic drawing similar to FIG. 1, indicating how the medical image data set is partitioned into slices.

FIG. 2 shows a schematic drawing similar to FIG. 1, indicating how the medical image data set is partitioned into slices as indicated by the equidistant horizontal lines within the rectangle illustrating the medical image data set 5. Shown to the right of the data set 5 is the result of the content aware analysis and recognition of this anatomical portion of a patient given by the names of the found organs. Thus, lungs (right and left), heart, spleen, kidneys and liver are shown adjacent to a double-arrowed line indicating the extent of the various organs in terms of slices. Notice that one slice may contain more than one organ. Additionally, one organ can be sub-divided into sub-parts, e.g. analysis and recognition of the heart can identify four chambers and identify each chamber as a right or left atrium or a right or left ventricle.

Figure 3:
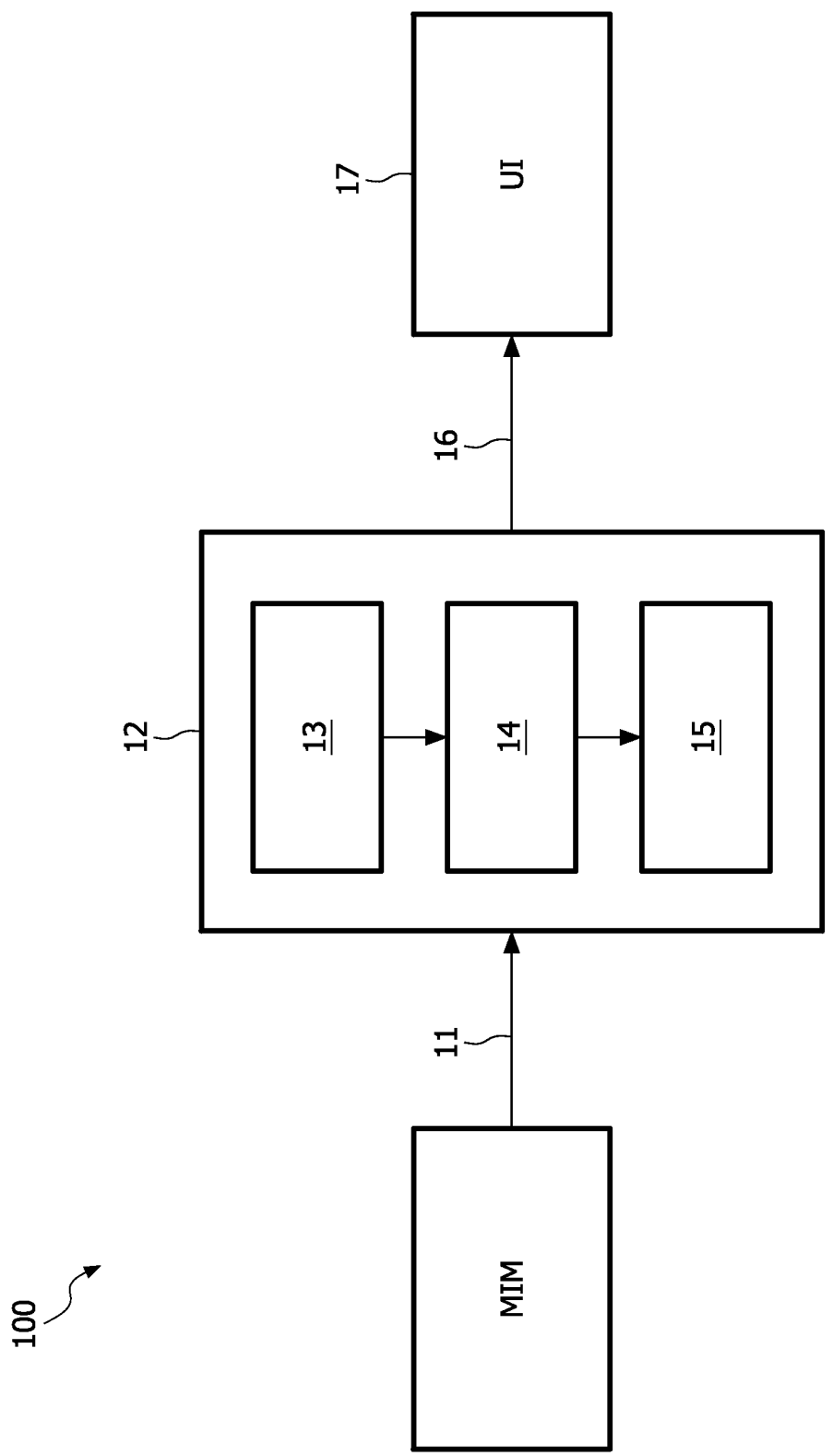
FIG. 3 shows a schematic drawing of an embodiment of the system of the invention, FIG. 4 schematically illustrates the association between indicators and respective pluralities of data slices.

FIG. 3 shows a schematic drawing of an embodiment of the retrieving system of the invention. The retrieving system 100 comprises an image acquisition apparatus MIM. The retrieving system 100 is arranged for retrieving slices of data from a medical image data set 5 acquired by the image acquisition apparatus MIM, using for example computer tomography (CT), magnetic resonance imaging (MRI), positron electron tomography (PET), single photon emission computed tomography (SPECT), ultrasound scanning, and rotational angiography, or any other medical imaging modality. The transmission from the modality MIM to the unit 12 can be via a dedicated connection means 11 (short range or long range, possibly via internet) or by wireless transmission.

The system 100 comprises segmenting means 13 for segmenting the medical image data set 5. The system 100 also comprises processing means 14 for associating an indicator with a plurality of slices, the indicator being representative of an object obtained in the segmentation. The object can for example be found from a content specific analysis with a semi-automated (i.e. with a user input) or completely automated anatomical recognition method on the segmented medical image data set 5. Thus, for example, the first object 1 can be the heart, and the second object 2 can be the lungs, cf. FIG. 4. Notice that any plurality of organs can be applied within the context of the present invention, the notion of a "first" and a "second" merely being for convenience of referral. Additionally, retrieval means 15 are provided for retrieving the plurality of data slices associated with an indicator when said indicator is selected. Notice that the plurality of data slices retrieved is typically less than the total medical image data set, thereby causing the need for data transfer to be reduced. The retrieval means 15 may also be partly or completely located near the user interface 17 (UI). The user input for selecting an indicator may typically come from the user interface 17 (UI). The indicators may be transferred for displaying via dedicated connection means 16 (short range or long range, possibly via internet) or by wireless transmission to the user interface (UI) 17 where a radiologist or similarly trained personnel can benefit from the improved retrieval capabilities provided by the present invention.

Figure 4:
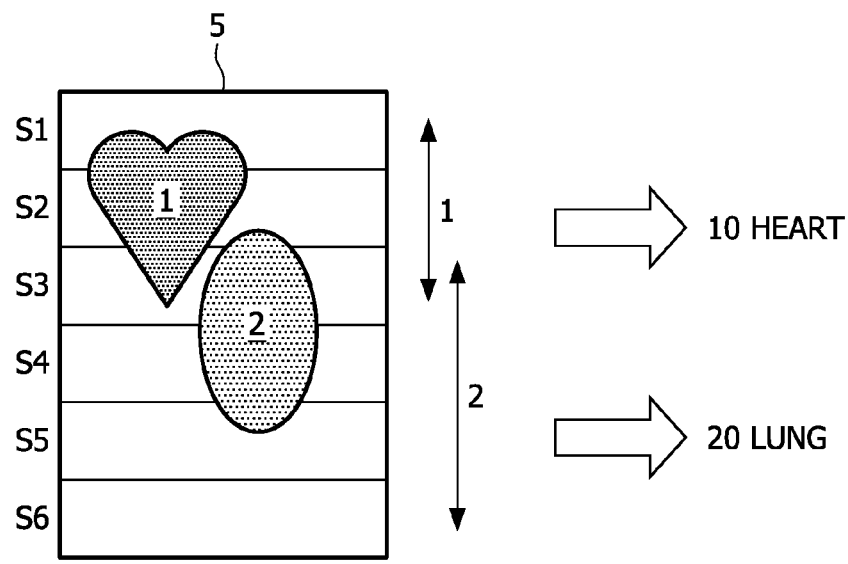

FIG. 4 schematically illustrates association between indicators and respective pluralities of data slices comprising, e.g., data defined by an object or an anatomically distinct region. FIG. 4 schematically shows segmented medical image data set 5 comprising slices S1, S2, S3, S4, S5, and S6. The segmentation of the medical image data set 5 reveals two objects: a heart 1 and a lung 2. In this illustrative example, the object 1 data, i.e. the heart data, is contained within slices S1, S2, and S3, whereas the other object 2 data, i.e. the lung data, is contained within the slices S2, S3, S4 and S5. When performing an association of an indicator with slices comprising the object data based on segmentation comprising a content specific analysis with a semi-automated/automated anatomical recognition method on the segmented medical image data 5 set, the association results in associating indicators 10 "HEART" and 20 "LUNG" with the heart 1 data and lung 2 data, respectively. When retrieving the data slices associated with the heart 1, there is no need for transferring all slices S1-S6, only slices S1-S3 need to be transferred (the number of slices being merely for illustrative purposes; under realistic conditions the total number of slices will typically be significantly higher and the number of retrieved slices will be a small fraction of that total number). In the exemplary embodiment illustrated in FIG. 4, indicators 10 and 20 are text indicators. Other indicators are also possible, as will be explained below.

Figure 5:
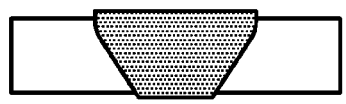
FIG. 5 shows a schematic drawing of various kinds of representative indicators.
Figure 5:
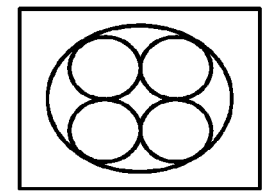
Figure 5:
Figure 5:
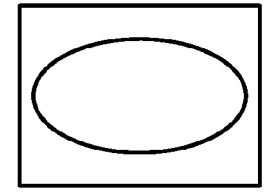

FIG. 5 shows a schematic drawing of various kinds of indicators 10 and 20. Like in FIG. 4, the indicator can be a text, preferably the name of the organ in a suitable language, i.e. HEART and LUNG, as is also shown in column A of FIG. 5. In another embodiment, the first and second indicator 10 and 20 can be a picture of the first 1 and the second 2 object, respectively, as shown in column B and C. Column B represents a side view of the slices, whereas column C represents a cross-sectional view, i.e. a multiplanar reformatted imaging of the original slices or an original slice of the acquired image data. The pictures are preferably thumbnail pictures or similar small pictures in order to improve the overview for a user. Additionally, a suitable symbol can be used as an indicator 10 or 20.

Figure 6:
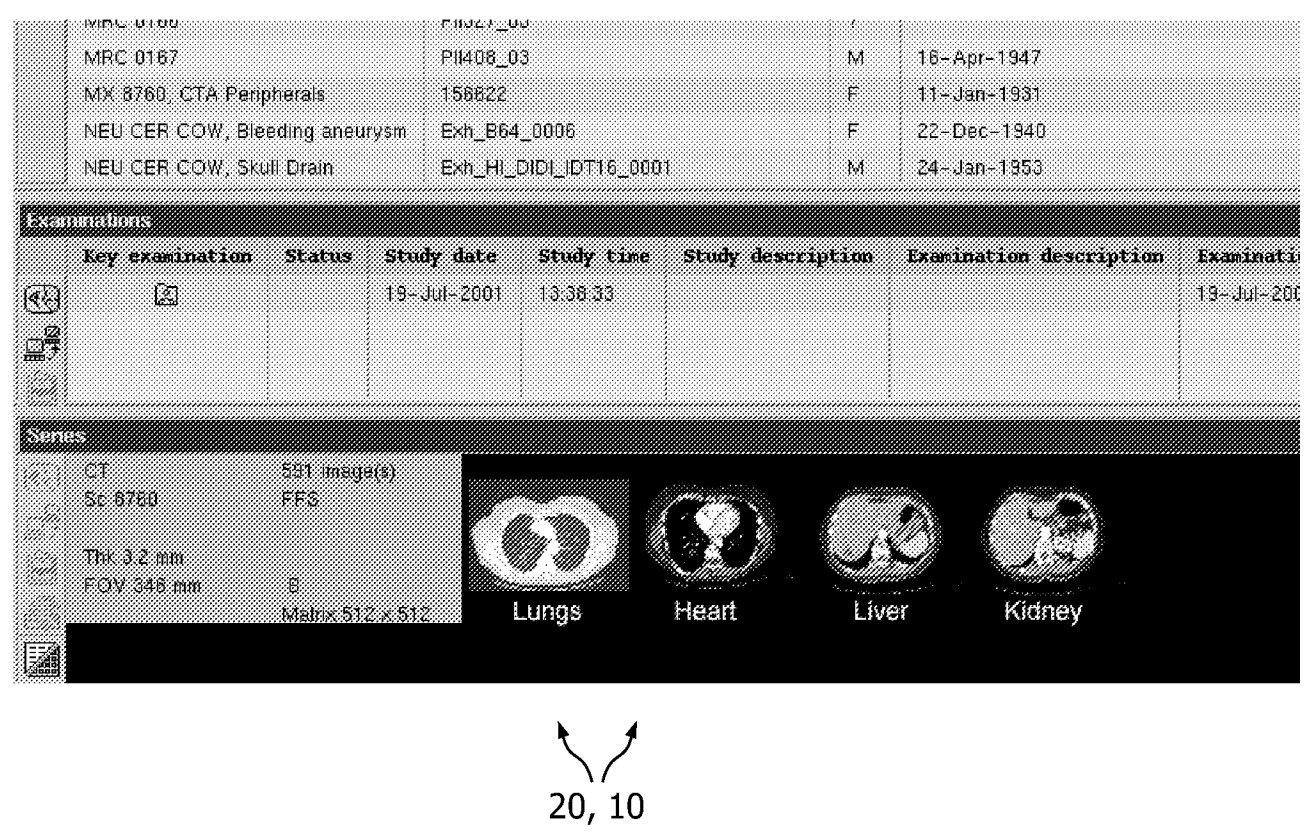

FIG. 6 illustrates a portion of a user interface UI according to the present invention with the indicators 10 and 20 representing the lungs and heart, respectively. Each indicator comprises a text label and a representative slice image.

Figure 7:
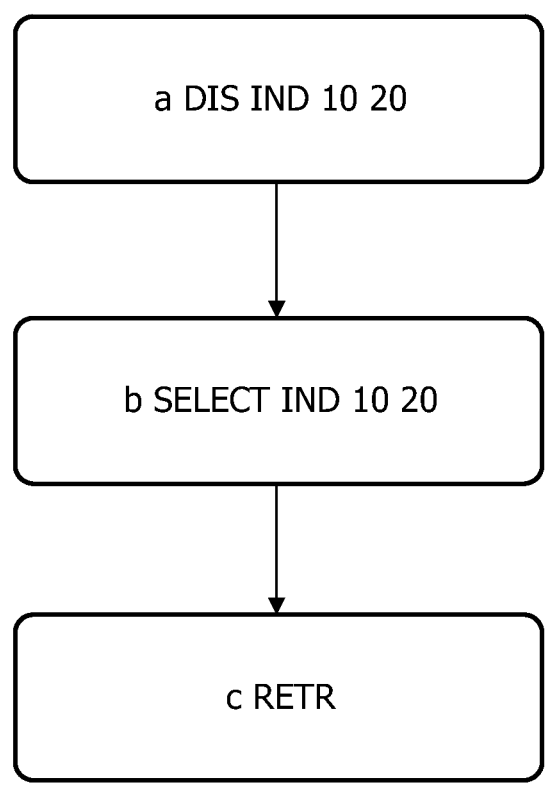
FIG. 7 shows a schematic flowchart of the method of retrieving a plurality of data slices from a medical image data set.

FIG. 7 shows a schematic flowchart of the method of retrieving a plurality of data slices from a medical image data set 5, the method comprising:

a) displaying an indicator 10 and 20 associated with the plurality of data slices;
b) selecting the indicator 10 and 20 based on a user input 17; and
c) retrieving the plurality of data slices associated with the indicator when said indicator is selected;

wherein the association between the indicator and the plurality of slices is based on segmentation of the medical image data set, the indicator representing an object obtained in the segmentation of the medical image data set, the plurality of data slices comprising the object data.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the verb "to comprise" and its conjugations do not exclude other possible elements or steps. Also, the use of the indefinite article "a" or "an" etc., should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is possible and advantageous.

The invention claimed is:

1. A method of retrieving a plurality of data slices from a medical image data set, the method comprising:
   a) displaying an indicator associated with the plurality of data slices;
   b) selecting the indicator based on a user input; and
   c) retrieving the plurality of data slices associated with the indicator when said indicator is selected;
   wherein the association between the indicator and the plurality of slices is based on segmentation of the medical image data set, the indicator representing an object obtained in the segmentation of the medical image data set, the plurality of data slices comprising the object data;
   wherein the indicator associated with the plurality of slices is selected from a table with pre-defined indicators and settings for creating the indicator.

2. The method according to claim 1, further comprising:
   segmenting the medical image data, thereby obtaining the object data;
   identifying slices comprising the object data, thereby creating the plurality of data slices;
   determining the indicator to be associated with the plurality of data slices; and
   associating the indicator with the plurality of data slices.

3. The method according to claim 1, wherein the object is an anatomically distinct region.

4. The method according to claim 1, wherein the object is found from a content specific analysis comprising an anatomical recognition method.

5. A system for retrieving a plurality of data slices from a medical image data set, the system comprising:
   a) a display, the display unit displaying an indicator associated with the plurality of data slices;
   b) a user interface device configured to receive a user input for selecting the indicator; and
   c) a retrieval unit configured to retrieve the plurality of data slices associated with the indicator when said indicator is selected;
   wherein the association between the indicator and the plurality of slices is based on segmentation of the medical image data set, the indicator representing an object obtained in the segmentation of the medical image data set, the plurality of data slices comprising the object data;
   wherein the indicator associated with the plurality of slices is selected from a table with pre-defined indicators and settings for creating the indicator;
   wherein the segmentation is based on the plurality of data slices.

6. The system according to claim 5, further comprising:
   a segmentation unit configured to segment the medical image data, thereby obtaining the object data;
   an identification unit configured to identify slices comprising the object data, thereby creating the plurality of data slices;
   a determination unit configured to determine the indicator to be associated with the plurality of data slices; and
   an association unit configured to associate the indicator with the plurality of data slices.

7. A system as claimed in claim 5 further comprising an image acquisition apparatus (MIM).

8. A computer program product embodied on a non-transitory computer readable medium and being adapted to enable a computer system comprising at least one computer having data storage means in connection therewith to control a computer system to perform a method of retrieving a plurality of data slices from a medical image data set, the method comprising:
   a) displaying an indicator associated with the plurality of data slices;
   b) selecting the indicator based on a user input; and
   c) retrieving the plurality of data slices associated with the indicator when said indicator is selected;
   wherein the association between the indicator and the plurality of slices is based on segmentation of the medical image data set, the indicator representing an object obtained in the segmentation of the medical image data set, the plurality of data slices comprising the object data;
   wherein the indicator associated with the plurality of slices is selected from a table with pre-defined indicators and settings for creating the indicator.

9. The method according to claim 1, wherein the principal axes is the moment of inertia tensor of the object.

10. The method according to claim 1, wherein the segmentation is based on a plurality of slices.

11. The method according to claim 1, wherein the segmentation is based on detecting a contour in an image computed from a single data slice.

12. The system according to claim 5, wherein the indicator is a representative picture computed from the plurality of slices.

13. The system according to claim 5, wherein the indicator is a representative text describing the plurality of slices.

14. The system according to claim 5, wherein the table further comprises a pre-defined list of symbols, each symbol having a generally accepted meaning in the field of medicine.

15. The system according to claim 12, wherein the representative picture comprises a thumbnail.

16. The system according to claim 5, wherein the indicator includes a cross-sectional view of the object defined by one or more principal axes of the object; wherein the cross-sectional view may be based on a slice chosen approximately from the middle of the plurality of data slices.

17. The system according to claim 16, wherein the principal axes is the moment of inertia tensor of the object.

18. The computer program product according to claim 8, wherein the segmentation is based on the plurality of data slices.

19. The computer program product according to claim 8, wherein the segmentation is based on detecting a contour in an image computed from a single data slice.

20. The method of claim 1, wherein the indicator includes a cross-sectional view of the object defined by one or more principal axes of the object and wherein the cross-sectional view is based on a slice chosen approximately from the middle of the plurality of data slices.

* * * * *